(12) United States Patent
Sim et al.

(10) Patent No.: US 11,702,681 B2
(45) Date of Patent: Jul. 18, 2023

(54) MUTANT STRAIN HAVING POLYHYDROXYBUTYRATE PRODUCTION ABILITY AND METHOD FOR PRODUCING POLYHYDROXYBUTYRATE USING THE STRAIN

(71) Applicant: Korea University Research and Business Foundation, Seoul (KR)

(72) Inventors: Sang Jun Sim, Seoul (KR); Hyejin Roh, Seoul (KR); Jeong Seop Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 17/564,601

(22) Filed: Dec. 29, 2021

(65) Prior Publication Data
US 2022/0205002 A1 Jun. 30, 2022

(30) Foreign Application Priority Data

Dec. 29, 2020 (KR) .......... 10-2020-0185509
Dec. 27, 2021 (KR) .......... 10-2021-0188836

(51) Int. Cl.
| | | |
|---|---|---|
| C12P 7/625 | (2022.01) | |
| C12N 1/20 | (2006.01) | |
| C12N 9/04 | (2006.01) | |
| C12N 9/10 | (2006.01) | |
| C12R 1/01 | (2006.01) | |

(52) U.S. Cl.
CPC .............. *C12P 7/625* (2013.01); *C12N 1/205* (2021.05); *C12N 9/0006* (2013.01); *C12N 9/1029* (2013.01); *C12Y 101/01036* (2013.01); *C12Y 203/01* (2013.01); *C12Y 203/01016* (2013.01); *C12R 2001/01* (2021.05)

(58) Field of Classification Search
CPC ....... C12P 7/625; C12N 1/205; C12N 9/0006; C12N 9/1029; C12Y 101/01036; C12Y 203/01; C12Y 203/01016; C12R 2001/01; C12R 2001/89
See application file for complete search history.

(56) References Cited

PUBLICATIONS

Durfee et al., Gen Bank accession No. B1X9L5, Dec. 2, 2020.*
Copeland et al., Gen Bank accession No. ABV94800, Jan. 28, 2014.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Lee et al., J. Agric. Food Chem. 65:10424-10428, Oct. 25, 2017.*
Peoples et al., GenBank accession No. J05003, 1993.*
Peoples et al. (GenBank accession No. J04987, 1993.*
Extended European Search Report dated Jul. 4, 2022 in counterpart European Patent Application No. 21217952.7 (7 pages in English).
Peoples, Oliver P., et al. "Poly-β-hydroxybutyrate (PHB) biosynthesis in Aicaligenes eutrophus H16: identification and characterization of the PHB polymerase gene (phbC)." *Journal of Biological Chemistry* vol. 264. Issue 26 (1989). pp. 15293-15297.
Roh, Hyejin, et al. "Improved CO2-derived polyhydroxybutyrate (PHB) production by engineering fast-growing cyanobacterium Synechococcus elongatus UTEX 2973 for potential utilization of flue gas." *Bioresource technology* vol. 327 (2021): 124789. pp. 1-9.
Suzuki, Taro, et al. "A recombinant cyanobacterium that accumulates poly-(hydroxybutyrate)." *Biotechnology letters* vol. 18. Issue 9 (1996). pp. 1047-1050.
Yu, Jingjie, et al. "Synechococcus elongatus UTEX 2973, a fast growing cyanobacterial chassis for biosynthesis using light and CO2." *Scientific reports* vol. 5 (2015): 8132. pp. 1-10.
Elhai, Jeff et al. "Conjugal Transfer of DNA to Cyanobacteria" Methods in Enzymology, Academic Oress, vol. 167, 1988, pp. 747-754.
Elhai, Jeff et al. "Reduction of Conjugal Transfer Efficiency by Three Restriction Activites of *Anabaena* sp. Strain PCC 7120" ASM Journals, Journal of Bacteriology, Jan. 31, 2021, (8 pages in English).
Chaogang, Wang et al. "Biosynthesis of POly-3-Hydroxybutyrate (PHB) in the Transgenic Green Alga *Chlamydomonas reinhardtii*", Journal of Phycology, 46: 396-402. 2010 (7 pages in English).
Drosg, Bernhard, et al. "Photo-autotrophic production of poly (hydroxyalkanoates) in cyanobacteria." *Chemical and Biochemical Engineering Quarterly* 29.2 (2015): 145-156.
Chwa, Jun-Won, et al. "Engineering of a modular and synthetic phosphoketolase pathway for photosynthetic production of acetone from CO 2 in S ynechococcus elongatus PCC 7942 under light and aerobic condition." Plant biotechnology journal 14.8 (2016): 1768-1776.

(Continued)

*Primary Examiner* — Delia M Ramirez
(74) *Attorney, Agent, or Firm* — NSIP Law (57) ABSTRACT

Disclosed is a mutant strain having the ability to produce polyhydroxybutyrate. The novel strain has a significantly high growth rate and an improved ability to produce PHB compared to existing PHB-producing cyanobacterial strains. Therefore, the novel strain is suitable for use in the production of PHB and the development of various products using PHB. In addition, the novel strain is useful as a photosynthetic strain for developing a PHB production process using industrial flue gas due to its ability to produce PHB from only $CO_2$ without any additional organic carbon source. Also disclosed is a method for producing polyhydroxybutyrate using the mutant strain.

12 Claims, 6 Drawing Sheets
Specification includes a Sequence Listing.

(56) References Cited

PUBLICATIONS

Abernathy, Mary H., et al. "Deciphering cyanobacterial phenotypes for fast photoautotrophic growth via isotopically nonstationary metabolic flux analysis." Biotechnology for biofuels 10.1 (2017): 1-13.

Ungerer, Justin, et al. "Adjustments to photosystem stoichiometry and electron transfer proteins are key to the remarkably fast growth of the cyanobacterium Synechococcus elongatus UTEX2973." MBio 9.1 (2018): e02327-17.

* cited by examiner

MUTANT STRAIN HAVING POLYHYDROXYBUTYRATE PRODUCTION ABILITY AND METHOD FOR PRODUCING POLYHYDROXYBUTYRATE USING THE STRAIN

Under the provisions of the Budapest Treaty on the International Recognition of the Deposit of Microorganisms for the Purpose of Patent Procedure, Applicant has deposited biological material comprising *Synechococcus* 2973-phaCAB strain with the International Depository Authority, Korean Collection for Type Cultures, 181, Ipsin-gil, Jeongeup-si, Jeolllabuk-do, 56212, Republic of Korea, on Dec. 28, 2020 under the accession number KCTC 14421BP. The deposited *Synechococcus elongatus* strain comprises *Synechococcus* 2973-phaCAB.

BACKGROUND OF THE INVENTION

1. Field of the Invention

The present invention relates to a mutant strain having the ability to produce polyhydroxybutyrate and a method for producing polyhydroxybutyrate using the same.

2. Description of the Related Art

The industry for the manufacture of petrochemical products, including plastics, accounts for 16% of global $CO_2$ emissions that have a major impact on climate change. Petroleum-based plastics cause issues such as landfilling of waste, threats to the marine ecosystem, and toxicity of microplastics due to their low degradability. Thus, a great deal of research has been devoted to sustainable and eco-friendly bioplastics that can replace existing plastics. Various raw materials for bioplastics are known. Polyhydroxybutyrate (PHB) has received particular attention as a biodegradable polymer that can replace widely used polypropylene (PP), a petroleum-derived polymer, due to its excellent mechanical properties such as high tensile strength. Polyhydroxybutyrate has high practical utility because of its high crystallinity and moisture resistance similar to those of PP and improved thermoplastic processability. The potential applicability of PHB can be greatly extended due to the biocompatibility of PHB compared to that of other petroleum-based plastics. The current industrial production of PHB mainly relies on microbial fermentation using corn or refined sugar. This fermentation process involves a high production cost and raises ethical issues regarding the use of food resources. Particularly, from an economic point of view, the high production cost of PHB compared to that of petroleum-based plastics is an obstacle to the industrialization of bioplastics.

PHB production using photosynthetic organisms under photoautotrophic conditions has attracted attention as an alternative to overcome this limitation (Chaogang et al., 2010, J. Phycol. 46 (2), 396-402). This strategy uses $CO_2$ as the sole carbon source, saving raw material costs as well as contributing to $CO_2$ reduction. Further cost saving can be expected when $CO_2$ is obtained from sustainable sources such as industrial flue gas. This expectation can be met by using various photosynthetic organisms, particularly cyanobacteria whose growth rate, photosynthetic efficiency, and $CO_2$ conversion are higher than those of transformed plants. For these reasons, most studies on photosynthetic PHB production have been conducted in cyanobacteria.

However, wild-type cyanobacteria known hitherto contain less than 10% of PHB under photoautotrophic conditions. The low productivity of wild-type cyanobacteria limits their industrial applications. Studies aimed at increasing PHB productivity have been conducted to overcome this limitation. For example, there have been many studies based on metabolic engineering in *Synechocystis* sp. PCC 6803, a typical PHB-producing strain. However, these studies are limited in increasing PHB content (Drosg et al., 2015, Chem. Biochem. Eng. Quarter. 29 (2), 145-156). Considering that biomass productivity is a key parameter affecting the productivity of final bioproducts, the main reason for low PHB productivity is because of the low biomass productivity in cyanobacterial strains such as *Synechocystis* sp. PCC 6803 that naturally synthesize PHB.

In this connection, *Synechococcus elongatus* UTEX 2973 (hereinafter referred to as simply *Synechococcus* 2973) has recently been reported as a strain whose growth rate surpasses those of other cyanobacterial strains. The photosynthetic rate and $CO_2$ uptake of *Synechococcus* 2973 were reported to be at least twice as high as those of other cyanobacterial strains (Abernathy et al., 2017, Biotechnol. Biofuels 10 (1), 1-13).

Under these circumstances, the present inventors have earnestly and intensively conducted research to develop a strain with an outstanding ability to produce PHB, and as a result, found that a novel strain generated by transformation of the phaCAB gene derived from *Cupriavidus necator* H16 into *Synechococcus elongatus* strain UTEX 2973 has a significantly improved ability to produce PHB compared to existing strains. The present invention has been accomplished based on this finding.

SUMMARY OF THE INVENTION

One object of the present invention is to provide a novel *Synechococcus elongatus* mutant strain that has an outstanding ability to produce polyhydroxybutyrate.

Another object of the present invention is to provide a method for producing polyhydroxybutyrate using the mutant strain.

In one aspect, the present invention provides a *Synechococcus elongatus* strain including the phaA gene encoding a β-ketothiolase, the phaB gene encoding an acetoacetyl-CoA reductase, and the phaC gene encoding a polyhydroxybutyrate (PHB) synthase.

According to the present invention, the gene phaA encoding a β-ketothiolase may include the sequence set forth in SEQ ID NO: 1.

According to the present invention, the gene phaB encoding an acetoacetyl-CoA reductase may include the sequence set forth in SEQ ID NO: 2.

According to the present invention, the gene phaC encoding a PHB synthase may include the sequence set forth in SEQ ID NO: 3.

According to the present invention, the strain may be *Synechococcus* 2973-phaCAB deposited under accession number KCTC14421BP.

In another aspect, the present invention provides a method for producing polyhydroxybutyrate (PHB) including culturing the *Synechococcus elongatus* strain.

According to the present invention, the culture may be performed under photoautotrophic conditions in which carbon dioxide or flue gas is supplied as a carbon source.

According to the present invention, the concentration of the carbon dioxide may be 4 to 6% (v/v).

According to the present invention, the culture may be performed at a light intensity of 10 to 600 µE $m^{-2}s^{-1}$.

According to the present invention, the culture may be performed at a temperature of 36 to 40° C.

The novel strain of the present invention has a significantly high growth rate and an improved ability to produce PHB compared to existing PHB-producing cyanobacterial strains. Therefore, the novel strain of the present invention is suitable for use in the production of PHB and the development of various products using PHB. In addition, the novel strain of the present invention is useful as a photosynthetic strain for developing a PHB production process using industrial flue gas due to its ability to produce PHB from only $CO_2$ without any additional organic carbon source.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1 shows (A) a schematic diagram of a plasmid used to confer the ability to produce PHB to Synechococcus strain 2973, in which the gene cluster phaCAB is introduced into the neutral site 1 (NSI) locus on the Synechococcus 2973 chromosome and primers used for PCR verification are indicated by the arrows and (B) PCR results for identifying completely segregated mutant strain Synechococcus 2973-phaCAB. Specifically, (B) shows PCR results for wild-type Synechococcus 2973 and mutant strain Synechococcus 2973-phaCAB to determine whether the PHB pathway was inserted into the neutral site I locus on the chromosome through homologous recombination. The target sizes of the PCR products for the wild type were as follows: NSI (1.0 kb) and phaCAB (no band). The target sizes of the PCR products for the mutant strain were as follows: NSI (7.7 kb) and phaCAB (4.0 kb). 1 kb DNA ladder from Elpis-biotech (Korea) was used as a marker;

DETAILED DESCRIPTION OF THE INVENTION

Unless otherwise defined, all technical and scientific terms used herein have the same meaning as commonly understood by one of ordinary skill in the art to which this invention belongs. In general, the nomenclature used herein is well known and commonly employed in the art.

Cyanobacteria are microorganisms that can produce energy through photosynthesis and fix carbon dioxide to produce metabolites. Prokaryotic cyanobacteria are easy to genetically engineer compared to eukaryotic microalgae and are thus advantageous in altering metabolic pathways or artificially regulating metabolites. Synthetic biology/metabolic engineering techniques based on genetic engineering have recently been introduced to Synechococcus elongatus in order to produce a variety of biofuel substitutes or chemical products through metabolic pathways that have not previously been reported.

The present inventors have succeeded in generating a new strain by introducing the phaCAB gene derived from Cupriavidus necator H16 into a Synechococcus elongatus strain as a species of cyanobacterium and demonstrating an outstanding ability of the new strain to produce PHB, achieving the present invention.

Accordingly, the present invention provides a Synechococcus elongatus strain including the phaA gene encoding a β-ketothiolase, the phaB gene encoding an acetoacetyl-CoA reductase, and the phaC gene encoding a polyhydroxybutyrate (PHB) synthase.

The gene phaA encoding a β-ketothiolase may include the sequence set forth in SEQ ID NO: 1.

The gene phaB encoding an acetoacetyl-CoA reductase may include the sequence set forth in SEQ ID NO: 2.

The gene phaC encoding a PHB synthase may include the sequence set forth in SEQ ID NO: 3.

The strain may be Synechococcus 2973-phaCAB deposited under accession number KCTC14421BP.

The present invention also provides a composition for PHB production including the Synechococcus elongatus strain or a culture product thereof as an active ingredient.

Since the strain of the present invention has an outstanding ability to produce PHB, as described above, the use of the strain or culture product thereof enables the production of PHB in high yield.

The culture product of the *Synechococcus elongatus* strain is not particularly limited as long as it can be used to produce PHB in high yield. As an example, the culture product may be a culture, culture supernatant or lysate of the strain or a fraction thereof. Specifically, the culture product may be a culture of the strain, a culture supernatant obtained by centrifugation of the culture of the strain, a lysate obtained by physical treatment or sonication of the strain or a fraction obtained by centrifugation or chromatography of the culture, the culture supernatant or the lysate.

The present invention also provides a method for producing polyhydroxybutyrate (PHB) including culturing the *Synechococcus elongatus* strain.

The culture is preferably performed under photoautotrophic conditions in which carbon dioxide or flue gas is supplied as a carbon source.

The carbon dioxide is supplied for phototrophic culture of the strain and its concentration is preferably 4 to 6% (v/v) but is not limited thereto.

The culture is preferably performed at a light intensity of 10 to 600 $\mu E\ m^{-2} s^{-1}$ but is not limited thereto.

The culture is performed at a temperature of 36 to 40° C., preferably 38° C.

The culture may be performed in the presence of isopropyl-β-D-thiogalactoside (IPTG).

In the Examples section that follows, the strain of the present invention was found to produce up to 420 mg/L (content 16.7%) of PHB, which is 2.4 times (based on the induction period) to 3.8 times (based on the culture period) larger than the amount of PHB produced in *Synechocystis* sp. PCC 6803, a typical PHB-producing strain. Therefore, the strain of the present invention is expected to be suitable for use in the production of PHB and the development of various products using PHB. In addition, the strain of the present invention is useful as a photosynthetic strain for developing a PHB production process using industrial flue gas due to its ability to produce PHB from only $CO_2$ without an additional organic carbon source.

EXAMPLES

The present invention will be more specifically explained with reference to the following examples. It will be evident to those skilled in the art that these examples are merely for illustrative purposes and are not to be construed as limiting the scope of the present invention. Therefore, the true scope of the present invention is defined by the appended claims and their equivalents.

Experimental Methods

Materials and Methods

Chemicals and Reagents

All chemicals were purchased from Sigma-Aldrich (St. Louis, USA). Taq polymerases, restriction enzymes, Gibson assembly mixes, and DNA ladders were purchased from Takara (Japan), Fisher Scientifics (Pittsburg, USA), New England Biolabs (Ipswich, USA), and Elpis-biotech (Korea), respectively.

Strain Generation

Plasmid and Strain Construction

*Escherichia coli* (*E. coli*) strain Top10 was used as a host for molecular cloning and *E. coli* strain HB101 was used for transformation of plasmids into the cyanobacteria. SyneBrick vector (pSe1Bb1s-GFP) designed for site-specific chromosomal recombination of exogenous genes was used as a plasmid backbone (Chwa et al., 2016, Plant Biotechnol. J. 14 (8), 1768-1776.). Since a plasmid must contain a bom site (oriT region) at its replication origin for conjugal transfer, the pUC replication origin was replaced by pBR322 replication origin through restriction enzyme cloning. The gfp sequence was removed and the phaCAB operon of *Cupriavidus necator* H16 was inserted into the plasmid by Gibson Assembly to generate pSe1Bb1s-bom-phaCAB. All plasmids and strains used are shown in Table 1.

TABLE 1

| Strain or plasmid | Relevant characteristics | Reference |
|---|---|---|
| Strains | | |
| *E. coli* Top 10 | F- merA Δ(mrr-hsdRMS-merBC) φlacZΔM15 ΔlacX74 nupG recA1 araD139 Δ(arn-len)7697 galE15 galK16 rpsL(StrR) endA1 λ- | Invitrogen |
| *E. coli* HB101 | F- merB mrr hsdS20(rB- mB-) recA13 leuB6 ara-14 proA2 lacY1 galK2 xyl-5 mtl-1 rpsL20(SmR) glnV44 λ- | Takara Co., Ltd. |
| *Cupriavidus necator* H 16 | Donor of phaA, phaB, and phaC genes | KCTC |
| *Synechococcus* 2973 | Wild type *Synechoccocus elongatus* UTEX 2973 | UTEX |
| *Synechocystis* 6803 | Wild type *Synechocystis* sp. PCC 6803 | PCC |
| *Synechococcus* 2973-phbCAB | phaA, phaB, and phaC integrated at NSI in UTEX 2973 genome | This study |
| Plasmids | | |
| pRL623 | Helper plasmid, Mob$_{ColK}$, Cm$^r$ | (Elhai et al., 1997) |
| pRL443 | Conjugal plasmid, IncP, Amp$^r$, Tet$^r$ | (Elhai et al., 1997) |

TABLE 1-continued

| Strain or plasmid | Relevant characteristics | Reference |
|---|---|---|
| pSe1Bb1s-GFP | pUC replication ori, Spc$^r$, LacI, P$_{tre}$, gfp, NSI target sites | (Chwa et al., 2016) |
| pSe1Bb1s-bom-GFP | pBR322 replication ori, Spc$^r$, LacI, P$_{tre}$, gfp, NSI target sites | This study |
| pSe1Bb1s-bom-phaCAB | pBR322 replication ori, Spc$^r$, LacI, P$_{tre}$, NSI target sites, phaCAB | This study |

Conjugation of *Synechococcus* 2973

First, conjugation was performed on *Synechococcus* 2973 by triparental mating referring to the method described in the literature (Elhai, and Wolk et al., 1988, Methods in Enzymology, Vol. 167, Elsevier, pp. 747-754.) because the strain is not naturally competent. Conjugal and helper *E. coli* strains were first generated by transformation of pRL443 and pRL623 (Elhai et al., 1997, J. Bacteriol. 179 (6), 1998-2005.) via electroporation into *E. coli* HB101, respectively. Then, target plasmid pSe1 Bb1s-bom-phaCAB was transformed into competent helper HB101. For triparental mating, the conjugal HB101 containing pRL443 and the helper HB101 containing both pRL623 and pSe1Bb1s-bom-phaCAB were cultured with appropriate antibiotics (ampicillin 50 μg mL$^{-1}$, chloramphenicol 25 μg mL$^{-1}$) overnight. 100 μL of each strain was washed twice with fresh Lysogeny broth (LB) to remove all antibiotics and resuspended in the same volume of LB. Next, the two strains were mixed together and incubated at room temperature for 30 min. The *E. coli* suspension was mixed with 200 μL of *Synechococcus* 2973 (OD$_{730}$≈0.4-0.6) and incubated at room temperature for additional 30 min. Next, the mixture was spread on a BG11+5% (v/v) LB agar plate covered with a 0.45 μm nitrocellulose filter (Millipore) and incubated at a temperature of 38° C. and a light intensity of 100 μE m$^{-2}$s$^{-1}$ for 24 h. Then, the nitrocellulose filter was transferred to a BG11 agar plate for colony screening containing an appropriate antibiotic (75 μgmL$^{-1}$ of spectinomycin). Colonies were observed 3-7 days after incubation at a temperature of 38° C. and a light intensity of 100 μE m$^{-2}$s$^{-1}$. For complete segregation of a mutant, the individual colonies were restreaked 3-4 times on new BG11 plates for colony screening and identified by polymerase chain reaction (PCR) (Table 2). The segregated mutant was named *Synechococcus* 2973-phaCAB and was deposited under accession number KCTC14421BP on Dec. 28, 2020 with the Biological Resource Center, Korea Research Institute of Bioscience and Biotechnology, which is an international depository recognized under the Budapest Treaty.

TABLE 2

| Primer name | Primer sequence (5'-3') |
|---|---|
| phaCAB-F | GACATCATAACGGTTCTGGC |
| phaCAB-R | TCTTTCGACTGAGCCTTTCG |
| NSI-F | TAGTCGCCGCAGTAGTGATG |
| NSI-R | CTCCAGCAAGCTAGCGATTT |

Culture Conditions for Lab-Scale Experiments

*Synechococcus* 2973 and *Synechocystis* 6803 were allowed to grow in BG-11 media supplemented with 10 mM HEPES-NaOH (pH 8.0). 50 μg mL$^{-1}$ of spectinomycin was added to the media for mutant growth. For PHB production, each strain was cultured under continuous fluorescent light conditions (200 μE m$^{-2}$s$^{-1}$) in a 250 mL shaking flask (130 rpm) whose headspace was supplied with 5% (v/v) CO$_2$. The temperatures were maintained at 38° C. and 30° C., which were optimal for *Synechococcus* 2973 and *Synechocystis* 6803, respectively. For *Synechococcus* 2973, 1 mM isopropyl-D-thiogalactopyranoside (IPTG) was added at OD$_{730}$≈0.4-0.6 to induce PHB synthesis. For nitrogen deprivation of *Synechocystis* 6803, cells grown in the complete BG-11 medium were transferred to a nitrogen-deprived BG-11 medium in the late exponential phase. The nitrogen-deprived BG-11 was prepared by removing NaNO$_3$ and replacing (NH$_4$)$_5$[Fe(C$_6$H$_4$O$_7$)$_2$] and Co(NO$_3$)$_2$·H$_2$O with equimolar FeC$_6$H$_5$O$_7$ and CoCl$_2$·6H$_2$O, respectively. Cells were inoculated at an initial OD$_{730}$ of 0.05 in all lab-scale experiments.

Culture Conditions Using Photobioreactor for Large-Scale Cultivation

Indoor Cultivation

10 L closed bubble column photobioreactors were used for indoor cultivation of cyanobacterial strains. Each photobioreactor was made of a polypropylene film (14 cm width×140 cm height) having a V-shaped bottom to prevent cell accumulation. For medium compositions, HEPES buffer was replaced with a bicarbonate buffer system whose final pH was adjusted to ~7.8-8.0 by sparging 5% CO$_2$ gas into a 30 mM potassium hydroxide solution in the photobioreactor for 12 h. To simulate an outdoor cultivation system, cells were cultured at a light intensity of 400 μE m$^{-2}$s$^{-1}$ on a 16 h light-8 h dark cycle. 5% CO$_2$ (v/v) was supplied at 0.1 vvm to the photobioreactor and the average temperature was maintained at 34° C. Cells were inoculated at an initial OD730 of 0.3.1 mM IPTG was added after 24 h of cultivation for induction.

Outdoor Cultivation Using Industrial Flue Gas

Flue gas (3-6% of CO$_2$, 11.99±0.73% of O$_2$, 21.72±3.72 ppm of NO$_x$, 1.43±4.03 ppm of CO, water vapor and dust) was supplied from a combined heat and power plant operated by Korea District Heating Corp. (Panggyo, Gyeonggi-do Province, South Korea). A pipeline was connected from a desulfurization unit to a greenhouse for cultivation. The gas was supplied at 0.1 vvm to the photobioreactor. The photobioreactor was scaled up to 3 L while maintaining its width/height ratio. Natural light was provided as the sole light source during outdoor cultivation and there were changes in light intensity (10-600 μE m$^{-2}$s$^{-1}$) during the daytime. The internal temperature of the greenhouse was 20-35° C. over the entire cultivation period. Cells were inoculated at an OD$_{730}$ of 0.5 and 1 mM IPTG was added after 24 h of cultivation.

Quantification of Dry Weight

To measure the dry cell weight of each cyanobacterial strain, first, a filter paper (Whatman, pore size 0.45 µm) was washed with deionized water (DI water) and dried at 60° C. overnight to completely remove water. 5 mL of the cell suspension was loaded into the pre-weighed dry filter and rinsed with deionized water to remove excess salts. The cell-loaded filter was dried overnight and weighed to determine the dry cell weight. The change in the weight of the filter paper corresponds to the dry cell weight per given cell volume.

Quantification of PHB

To measure the concentration of PHB, first, chloroform and methanol containing 15% (v/v) $H_2SO_4$ were added to lyophilized cells, followed by incubation at 100° C. for 140 mM. Thereafter, DI water was added for phase separation. The methyl ester-containing organic (bottom) phase was analyzed for PHB using a gas chromatography-mass spectrometer (GC-MS, Agilent, 6890/5975) with a DB-WAX capillary column (30 m×250 µm×0.5 µm). GC configuration parameters were programmed as follows: split ratio 1:20, injection temperature 250° C., flow rate 0.7 mL $min^{-1}$, column oven temperature 80° C. for 2 min, temperature ramp of 10° C. $min^{-1}$, and 245° C. for 1 min. The mass spectrometer was programmed as follows: electron impact (EI) mode 70 eV, ion source temperature 215° C., and scan mass range 20-200. Methyl benzoate was used as an internal standard and poly((R)-3-hydroxybutyric acid) (Sigma-Aldrich, USA) was used for calibration curve determination.

Quantification of Glycogen

The cell suspension was collected by centrifugation, and the pellets were resuspended in 300 µL of 30% KOH and incubated at 100° C. for 90 min. Glycogen was precipitated by adding ice-cold ethanol to a final concentration of 70-75% (v/v), followed by incubation on ice for 2 h. The glycogen was collected by centrifugation. Subsequently, the pellets were washed with 70% and 98% (v/v) ethanol and dried until the residual ethanol was evaporated. Each pellet was resuspended in 300 µL of a sodium acetate solution (100 mM, pH 4.75) and amyloglucosidase (4 U $assay^{-1}$) was added thereto to enzymatically hydrolyze the glycogen to glucose. Incubation was performed at 60° C. for 2 h. After centrifugation, the glycogen content of the supernatant was determined using a glucose assay kit (Sigma-Aldrich, USA) according to the manufacturer's protocol.

Observation of PHB Granules by Transmission Electron Microscopy (TEM)

After removal of the medium by centrifugation, cells were fixed in 2% glutaraldehyde-2% paraformaldehyde in a 0.1 M phosphate buffer (pH 7.4) for 12 h, washed with a 0.1 M phosphate buffer, followed by postfixation with 1% $OsO_4$ in a 0.1 M phosphate buffer for 2 h. The fixed sample was dehydrated in a series of ethanol solutions (50, 60, 70, 80, 90, 95, and 100%) for 10 min each and infiltrated with propylene oxide for 10 min. The samples were then embedded using a Poly/Bed 812 kit (Polysciences), polymerized in an electron microscope oven (TD-700, DOSAKA, Japan) at 65° C. for 12 h, cut into 200 nm semi-thin sections, and stained with toluidine blue. The treated samples were placed on a copper grid, doubly stained with 3% uranyl acetate for 30 min and 3% lead citrate for 7 min, and imaged using a transmission electron microscope (JEM-1011, JEOL, Tokyo, Japan) with a Megaview III CCD camera (Soft imaging system-Germany) at 80 kV.

RNA Extraction and Real-Time qPCR

The cell suspension was centrifuged and the cell pellets were immediately frozen in liquid nitrogen. The frozen cells were homogenized in a lysis buffer and total RNA was extracted with a PureHelix™ Total RNA Purification Kit (Nanohelix, South Korea) according to the manufacturer's instructions. The total RNA was purified to remove gDNA contamination and reverse transcribed using a QuantiTect Reverse Transcription kit (Qiagen, USA) according to the manufacturer's instructions. The resulting cDNA was used as a template for subsequent real-time qPCR analysis. Quantitative real-time PCR was performed using a QuantiFast SYBR Green PCR kit (Qiagen, USA) on a Rotor-Gene Q pure detection system (Qiagen, USA). Reference genes for *Synechococcus* 2973 and *Synechocystis* 6803 were 16S rRNA and rnpB, respectively. Primers used are shown in Table 3. The fold change in gene expression relative to the control was calculated by the equation: Relative expression level (fold change)=$2^{-\Delta\Delta C_T}$.

TABLE 3

| Genes | Primer sequence (5'-3') |
|---|---|
| *Synechococcus* 2973-phaCAB | |
| phaA | For: ACGTTGTCATCGTATCCGCC<br>Rev: ATGACTTCGCTCACCTGCTC |
| phaB | For: CGACAAGGTCAAGTCCGAGG<br>Rev: GCTTGGTGACGTTGAACAGC |
| phaC | For: CAGCTGTTGCAGTACAAGCC<br>Rev: GTATGTCCCTGCTCCACCAC |
| 16S rRNA | For: GAATCTGCCTACAGGACGGG<br>Rev: AGCTACTGATCGTCGCCTTG |
| *Synechocystis* 6803 | |
| phaA | For: GCAATTGATTCCCCGGCAAG<br>Rev: AGCCCGGATGGTTAAAGCTG |
| phaB | For: CTTTGGCGATCCGGGAAGAT<br>Rev: TACTGGCTACGGGGAAAGT |
| phaC | For: ACATCCAGGTGGGCTTTACC<br>Rev: AAATCCACCATGTAGGGGCG |
| phaE | For: ATTATTGCGGGCCTTTGACG<br>Rev: CCCGGGCCAGTAAATCTTCC |
| rnpB | For: GGTACTGGCTCGGTAAACCC<br>Rev: GGCACCCTTGGGGAGTTATC |

Results and Discussion

Figure 1:
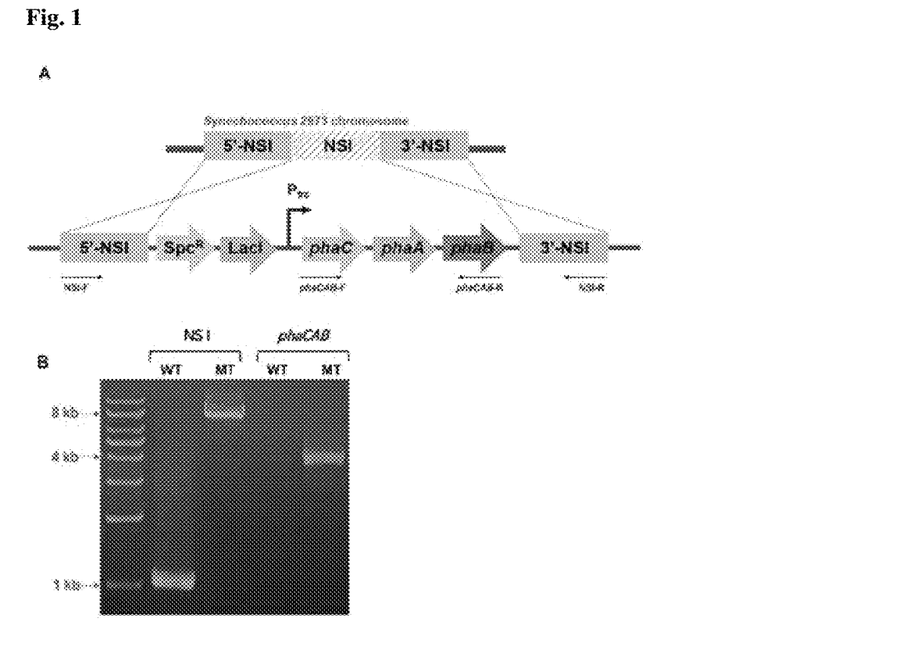
Figure 6:
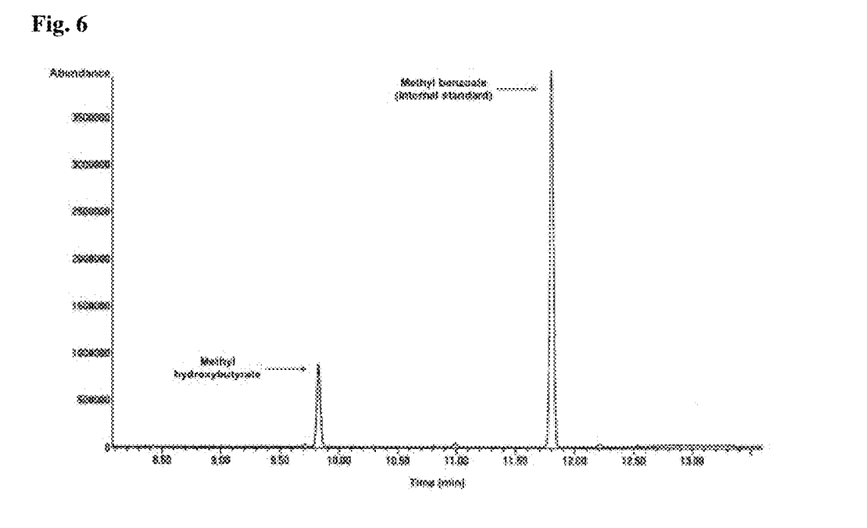
FIG. 6 is a GC-MS spectrum confirming the synthesis of PHB in Synechococcus 2973-phaCAB.
Figure 7:
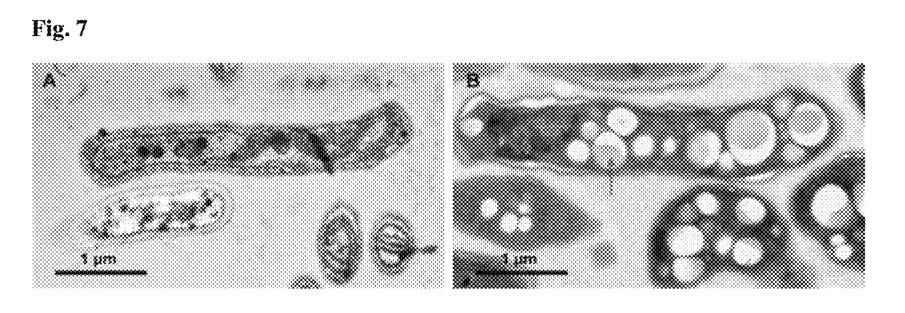
FIG. 7 shows TEM images of (A) wild-type Synechococcus 2973 and (B) mutant strain Synechococcus 2973-phaCAB for visual confirmation of PHB synthesis. The red arrow indicates an example of intracellular PHB granules.

Construction and Validation of Novel Mutant Strain *Synechococcus* 2973-phaCAB To develop PHB-producing *Synechococcus* strain 2973, the PHB synthesis pathway from *Cupriavidus necator* H16 was introduced into *Synechococcus* 2973 through conjugation. Given that *Synechococcus* 2973 grows three times faster than *Synechococcus* 7942 despite 99.8% similarity in their genomes (Ungerer et al., 2018, mBio 9 (1). expression of the PHB pathway in *Synechococcus* 2973 was expected to drastically improve the PHB productivity. In the present invention, the phaCAB operon was cloned into the neutral site I (NSI)-targeting plasmid and expressed under the IPTG-inducible strong promoter $P_{trc}$. The completely segregated transformant (hereinafter referred to as *Synechococcus* 2973-phaCAB) was identified by PCR using the primers shown in Table 1 (B of FIG. 1). Since *Synechococcus* 2973 does not naturally accumulate PHB, the synthesis of PHB via the exogenous pathway was verified by GC-MS analysis. The methanolized sample of *Synechococcus* 2973-phaCAB yielded a significant peak at a retention time (9.827 min) similar to that of the methanolized commercial PHB standard. This peak was not found in the wild type (*Synechococcus* 2973) (FIG. 6). A visual observation of PHB was further made through transmission electron microscopy (TEM). PHB granules were observed in the cells of the mutant (*Synechococcus* 2973-phaCAB) that were grown for 8 days of photoautotrophic cultivation (FIG. 7), unlike in the cells of wild type that were grown for the same period.

Characterization of Novel Mutant Strain *Synechococcus* 2973-phaCAB

Figure 2:
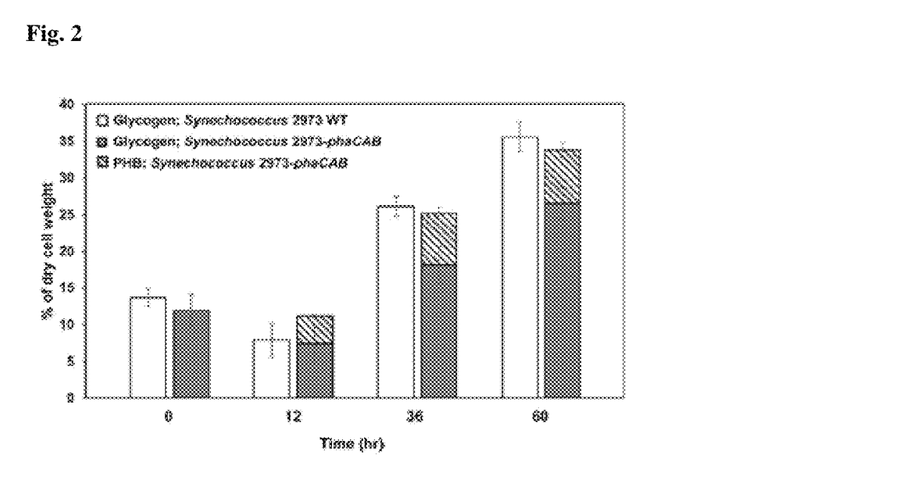
FIG. 2 compares the proportions of carbon reserves in wild-type Synechococcus 2973 and mutant strain Synechococcus 2973-phaCAB. The x-axis shows the time since IPTG induction.

First, an experiment was conducted to determine the viability of the mutant strain *Synechococcus* 2973-phaCAB by comparing the growth of the inventive mutant strain *Synechococcus* 2973-phaCAB with that of the wild type. As a result, the average biomass productivities in the wild type and the mutant strain were 0.535 g $L^{-1}d^{-1}$ and 0.472 g $L^{-1}d^{-1}$, respectively, under the conditions of 38° C., 200 µE $m^{-2}s^{-1}$, and 5% $CO_2$, and the average growth rates of the wild type and the mutant strain were 0.843 $d^{-1}$ and 0.813 $d^{-1}$, respectively (data not shown) under the same conditions. These results confirmed that the biomass accumulation in the mutant was slightly reduced but the growth was not inhibited by the synthesis of intracellular products. Next, the carbon utilization of the inventive mutant strain was characterized based on the glycogen content in order to understand how the inventive mutant strain accumulated a large amount of PHB, as in the TEM results. To this end, the glycogen and PHB contents of the mutant strain were observed for 60 h after IPTG induction of the PHB genes and were compared with those of the wild type grown for the same period of time (FIG. 2). As a result, the glycogen contents of the wild type and the mutant strain in the early stage of PHB induction were similar to each other. The glycogen content of the wild type steadily increased up to 35% of the dry cell weight over time, whereas the glycogen content of the mutant strain was as relatively low as 26% of the dry cell weight at 60 h. The glycogen contents of the wild type and the mutant strain were reduced at 12 h, which appear to be as a result of the slow glycogen accumulation compared to the fast biomass accumulation. PHB accumulated up to 7% of the dry cell weight at 60 h and the sum of the PHB and glycogen contents of the mutant strain was similar to the glycogen content of the wild type. These results suggest that the carbon flux is shared between glycogen and PHB for carbon storage in the mutant strain. Quantification of the glycogen and PHB contents revealed that the expression of phaCAB by the trc promoter can efficiently redirect the flux from the original carbon sink to PHB even without any additional metabolic pathway or optimization.

Figure 3:
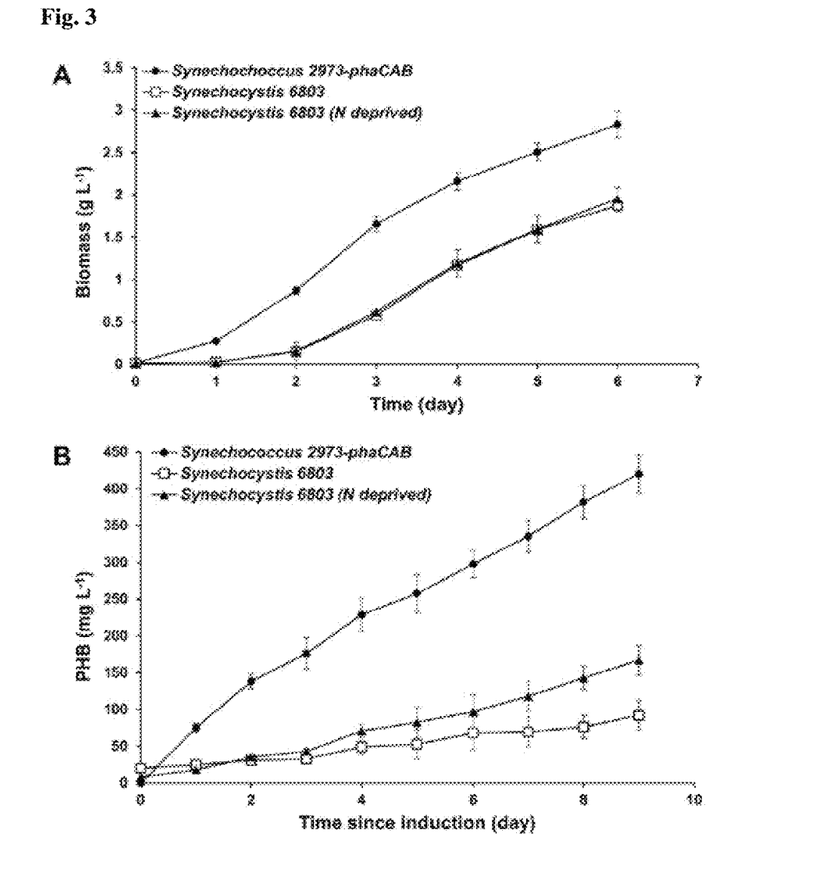
FIG. 3 shows (A) biomass accumulations and (B) PHB accumulations of Synechococcus 2973-phaCAB and Synechocystis 6803 in complete media and Synechocystis 6803 in nitrogen deprived media. Each x-axis shows the number of days since IPTG addition or replacement with nitrogen-deprived media.
Figure 8:
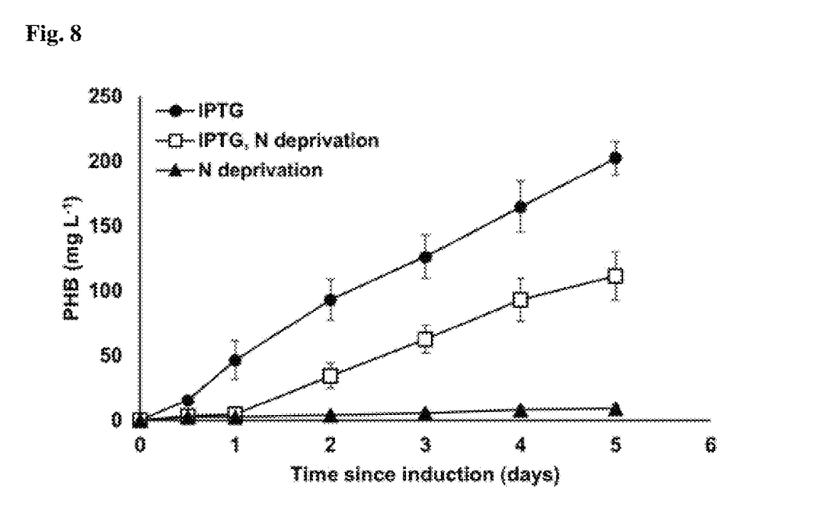
FIG. 8 shows PHB accumulations of Synechococcus 2973-phaCAB under various induction conditions (1 mM IPTG, 1 mM IPTG/nitrogen (N) deprivation, and nitrogen (N) deprivation). To prevent the inhibition of growth upon nitrogen deprivation, cells in the late exponential phase (on day 4 after culture) were exposed to nitrogen-deprived media. IPTG addition was also performed simultaneously to compare the effects of IPTG and nitrogen deprivation on PHB production.

Photoautotrophic Production of PHB in Novel Mutant Strain *Synechococcus* 2973-phaCAB First, the volumetric PHB accumulation of the inventive mutant strain *Synechococcus* 2973-phaCAB was compared with that of *Synechocystis* 6803, a cyanobacterial strain that is capable of naturally producing PHB. In addition, the growths of the mutant strain *Synechococcus* 2973-phaCAB and *Synechocystis* 6803 and the PHB accumulations and productivities in the two strains were evaluated using 5% $CO_2$ as the sole carbon source in order to investigate the potential applicabilities of the two strains in flue gas environments. For *Synechocystis* 6803, (1) cells grown in the complete BG11 medium relying on self-limitation of macronutrients and (2) cells grown in the nitrogen deprived medium were both observed. Because the early cell growth can be significantly suppressed in the nutrient deprived environment, a two-step cultivation was applied for the latter case, in which cells were transferred to the nitrogen deprived medium after sufficient growth of cells. As nitrogen deprivation was shown to have marginal effect on PHB induction in *Synechococcus* 2973-phaCAB (FIG. 8), *Synechococcus* 2973-phaCAB was investigated only in the complete BG11 medium supplemented with IPTG. As a result of comparing the growth performances of the two strains, the inventive mutant strain *Synechococcus* 2973-phaCAB showed high growth as expected (A of FIG. 3). The average biomass productivity in *Synechococcus* 2973-phaCAB was 0.469 g $L^{-1}d^{-1}$, which was 1.5 times higher than those in *Synechocystis* 6803 (0.310 g $L^{-1}d^{-1}$ and 0.323 gg $L^{-1}d^{-1}$ in the complete and nitrogen deprived media, respectively). The maximum specific growth rate of *Synechococcus* 2973-phaCAB was 2.67 $d^{-1}$, which was significantly higher than those of *Synechocystis* 6803 (1.65 $d^{-1}$ and 1.77 $d^{-1}$ in the complete and nitrogen deprived media, respectively). As the faster growth of *Synechococcus* 2973-phaCAB was confirmed, the PHB accumulation in *Synechococcus* 2973-phaCAB after the time of induction was compared with that in *Synechocystis* 6803. The results are shown in B of FIG. 3. Specifically, 1 mM IPTG was first added after 1 day of culture to induce the phaCAB operon in *Synechococcus* 2973-phaCAB. 6 days after culture, the medium was replaced with nitrogen deprived BG11 to induce PHB synthesis in *Synechocystis* 6803. *Synechocystis* 6803 grown in the complete BG11 medium relying on self-limitation of nitrogen was also compared. The volumetric PHB titer of *Synechococcus* 2973-phaCAB 9 days after induction (i.e. 10 days after culture) was 420 $mgL^{-1}$, representing 16.7% of the dry cell weight. Meanwhile, the volumetric PHB titer of *Synechocystis* 6803 9 days after induction (i.e. 15 days after culture) was 167 $mgL^{-1}$ under nitrogen deprivation conditions. Only 92 $mgL^{-1}$ of PHB accumulated in *Synechocystis* 6803 without nitrogen deprivation, demonstrating that nitrogen deprivation induction is effective for *Synechocystis* 6803. When the average PHB productivities after induction were compared, *Synechococcus* 2973-phaCAB was able to accumulate 46.7 mg $L^{-1}d^{-1}$ of PHB, which was found to be 4.6-fold and 2.4-fold higher than *Synechocystis* 6803 (10.2 mg $L^{-1}d^{-1}$) and nitrogen-deprived *Synechocystis* 6803 (18.6 mg $L^{-1}d^{-1}$), respectively. From these results, it can be seen that since induction for *Synechocystis* 6803 was started after 6 days of culture in order to prevent the inhibition of cell growth, an actual difference in PHB productivity between *Synechococcus* 2973-phaCAB and nitrogen-deprived *Synechocystis* 6803 would be much larger considering the entire culture period. Moreover, *Synechocystis* 6803 accumulated PHB after a long lag phase of ~3 days, whereas Synechococcus 2973-phaCAB could readily accumulate a considerable amount of PHB immediately after induction. Synechococcus 2973-phaCAB actually showed the highest specific PHB productivity (75 mg $L^{-1}d^{-1}$) on the first day of induction. These results concluded that the inventive mutant strain Synechococcus 2973-phaCAB is greatly advantageous in terms of PHB productivity due to its ability to produce a large amount of PHB starting from the early exponential phase.

Comparison of Relative Expression Levels of PHB Genes in Synechococcus 2973-phaCAB and Synechocystis 6803

Figure 4:
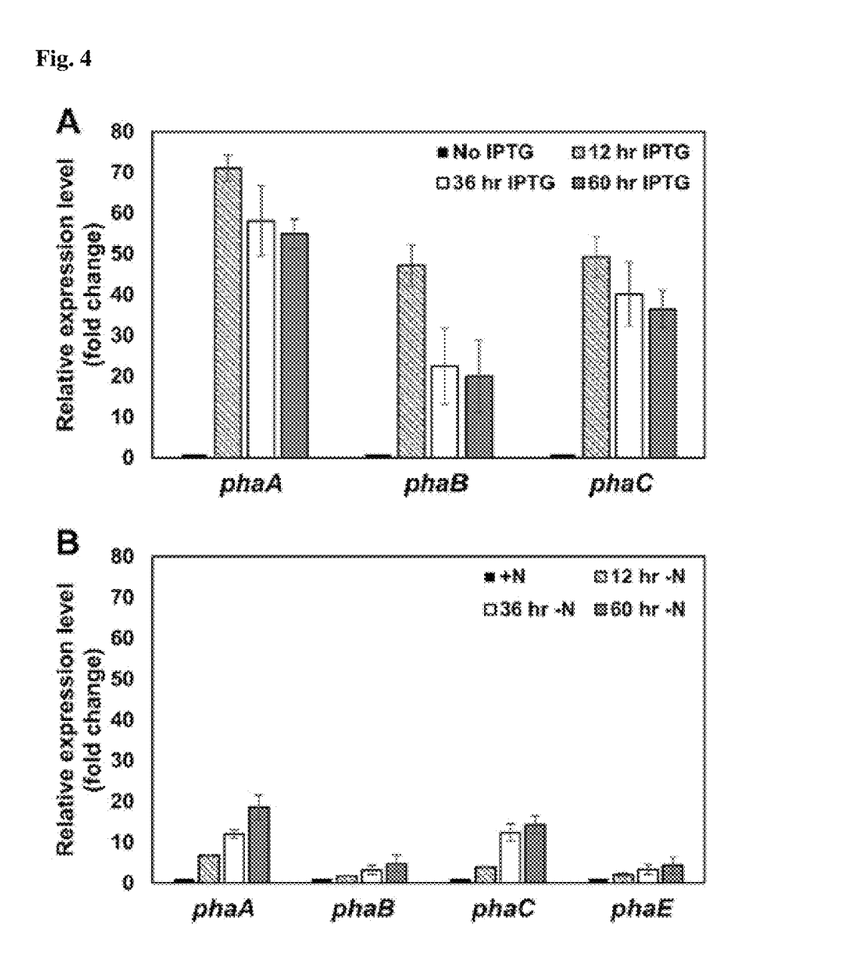
FIG. 4 shows the relative transcriptional expression levels of genes involved in PHB synthesis in Synechococcus 2973-phaCAB and Synechocystis 6803. A: relative expression levels of the phaA, phaB, and phaC genes in Synechococcus 2973-phaCAB since IPTG induction. The expression levels were normalized to the reference gene 16S rRNA and their fold changes were compared with the expression levels before IPTG induction. B: relative expression levels of the phaA, phaB, phaC, and phaE genes in Synechocystis 6803 after transfer to nitrogen-deprived media. The expression levels were normalized to the reference gene rnpB and their fold changes were compared with the expression levels before nitrogen deprivation.

Next, the expression levels of mRNAs involved in PHB synthesis were evaluated by qRT-PCR using the primers shown in Table 3. The transcriptional expression levels of the phaA, phaB, and phaC genes in Synechococcus 2973-phaCAB were investigated for 60 h after IPTG induction (A of FIG. 4) and the transcriptional expression levels of the phaA, phaB, phaC, and phaE genes in Synechococcus 6803 were investigated during the same period after transfer to nitrogen-depleted media (B of FIG. 4). In Synechococcus 2973-phaCAB, all three genes under control of the trc promoter were highly upregulated by IPTG addition. The greatly increased expression levels 12 h after induction were reflected by the highest specific PHB productivity (75 mg $L^{-1}d^{-1}$) achieved on the first day of induction. The decreased expression levels over time could be attributed to the consumption of IPTG in the media but the expression levels were still maintained very high. In contrast, the PHB genes in Synechocystis 6803 were not effectively upregulated by nitrogen deprivation, which can reflect their relatively low PHB accumulation capacities. More importantly, the expression levels of the PHB genes in Synechocystis 6803 showed a tendency to increase slowly but steadily over time, in contrast to the greatly increased expression levels in Synechococcus 2973-phaCAB. This gradual responses of the PHB genes to nitrogen deprivation are believed to be induced by the cells' primary responses in glycogen synthesis, resulting in slow PHB accumulation in the early stage of nitrogen deprivation. In contrast, the inventive mutant strain Synechococcus 2973-phaCAB can effectively accumulate a large amount of PHB without upregulation of genes associated with other competing metabolites because induction of the PHB genes does not rely on limitation of nutrients.

PHB production in Large-Scale Cultivation Conditions

Figure 5:
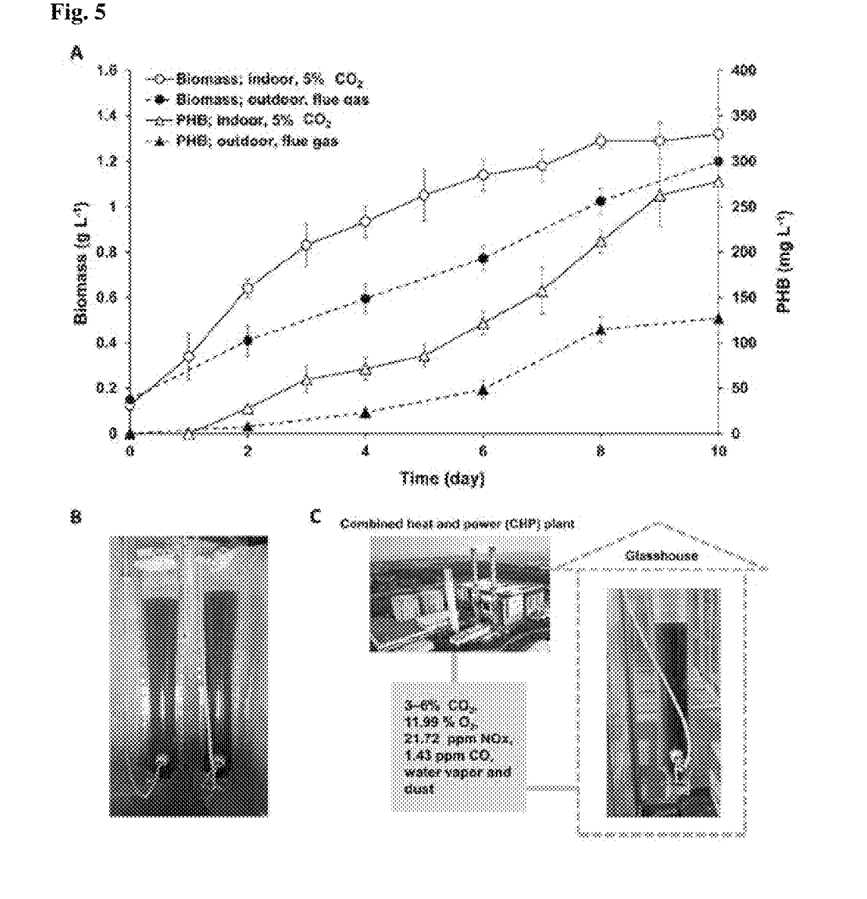
FIG. 5 shows the productions of PHB by cultivation in large-scale photobioreactors. A: biomass accumulations and PHB accumulations of Synechococcus 2973-phaCAB during indoor cultivation using 5% $CO_2$ (v/v) and outdoor cultivation using industrial flue gas as the sole carbon source, B: image of the photobioreactors used for indoor cultivation, and C: schematic of the photobioreactor, the industrial flue gas source for outdoor cultivation, and the composition of the industrial flue gas.

Synechococcus 2973-phaCAB showed a significantly high PHB productivity at lab scale. Thus, an experiment was conducted to further investigate scalability and performance for indoor and outdoor cultivation in large-scale photobioreactors. As shown in A of FIG. 5, the highest volumetric PHB titer achieved during 10 days of culture was 278 mg $L^{-1}$ corresponding to 21.1% of the dry cell weight. The volumetric PHB productivity and biomass productivity during the observed cultivation period were 27.8 mg $L^{-1}d^{-1}$ and 0.122 g $L^{-1}d^{-1}$, respectively. The decrease in total biomass concentration compared to that of the lab-scale experiment is believed to be due to the shading effect of the photobioreactors. Surprisingly, the PHB content (21.1% of the dry cell weight) after 10 days of culture was significantly higher than that in the lab-scale experiment(16.7% of the dry cell weight), indicating that the PHB accumulation was maintained high despite the reduced biomass accumulation. These results also indicate that the performance of Synechococcus 2973-phaCAB in terms of PHB accumulation can be reasonably maintained in indoor photobioreactors. The PHB production performance of Synechococcus 2973-phaCAB was further investigated under outdoor cultivation conditions using flue gas from an LNG power plant. Flue gas from a combined heat and power (CHP) plant in Korea was directly utilized as the sole carbon source. A place for outdoor cultivation and the composition of the flue gas are schematically shown in C of FIG. 5. As a result of the investigation, it was possible to achieve a volumetric PHB titer of 127 mg $L^{-1}$ over 10 days of culture. The volumetric PHB titer represents a volumetric PHB productivity of 12.7 mg $L^{-1}d^{-1}$ and a PHB content corresponding to 10.5% of the dry cell weight (A of FIG. 5). These results demonstrated that the inventive mutant strain Synechococcus 2973-phaCAB can be usefully applied to a large-scale PHB production process using industrial flue gas.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

Accession Number

Name of depository: Korea Research Institute of Bioscience and Biotechnology

Accession number: KCTC14421BP

Date of Deposit: Dec. 28, 2020

---

What is claimed is:

1. A *Synechococcus elongatus* strain comprising a phaA gene encoding a β-ketothiolase, a phaB gene encoding an acetoacetyl-CoA reductase, and a phaC gene encoding a polyhydroxybutyrate (PHB) synthase, wherein the *Synechococcus elongatus* strain is *Synechococcus* 2973-phaCAB deposited under accession number KCTC14421BP.

2. The *Synechococcus elongatus* strain according to claim 1, wherein the gene phaA encoding a β-ketothiolase comprises the sequence set forth in SEQ ID NO: 1.

3. The *Synechococcus elongatus* strain according to claim 1, wherein the gene phaB encoding an acetoacetyl-COA reductase comprises the sequence set forth in SEQ ID NO: 2.

4. The *Synechococcus elongatus* strain according to claim 1, wherein the gene phaC encoding a PHB synthase comprises the sequence set forth in SEQ ID NO: 3.

5. A method for producing polyhydroxybutyrate (PHB) comprising culturing the *Synechococcus elongatus* strain according to claim 1.

6. The method according to claim 5, wherein the culturing is performed under photoautotrophic conditions in which carbon dioxide or flue gas is supplied as a carbon source.

7. The method according to claim 6, wherein the concentration of the carbon dioxide is 4 to 6% (v/v).

8. The method according to claim 6, wherein the culturing is performed at a light intensity of 10 to 600 μE $m^{-2}s^{-1}$.

9. The method according to claim 6, wherein the culturing is performed at a temperature of 36 to 40° C.

10. A method for producing polyhydroxybutyrate (PHB) comprising culturing the *Synechococcus elongatus* strain according to claim 2.

11. A method for producing polyhydroxybutyrate (PHB) comprising culturing the *Synechococcus elongatus* strain according to claim 3.

12. A method for producing polyhydroxybutyrate (PHB) comprising culturing the *Synechococcus elongatus* strain according to claim 4.

\* \* \* \* \*

SEQUENCE LISTING

```
<160> NUMBER OF SEQ ID NOS: 3

<210> SEQ ID NO 1
<211> LENGTH: 1182
<212> TYPE: DNA
<213> ORGANISM: Artificial Sequence
<220> FEATURE:
<223> OTHER INFORMATION: gene coding beta-ketothiolase (phaA)

<400> SEQUENCE: 1
atgactgacg ttgtcatcgt atccgccgcc cgcaccgcgg tcggcaagtt tggcggctcg      60
ctggccaaga tcccggcacc ggaactgggt gccgtggtca tcaaggccgc gctggagcgc     120
```

| | |
|---|---|
| gccggcgtca agccggagca ggtgagcgaa gtcatcatgg ccaggtgct gaccgccggt | 180 |
| tcgggccaga accccgcacg ccaggccgcg atcaaggccg gcctgccggc gatggtgccg | 240 |
| gccatgacca tcaacaaggt gtgcggctcg ggcctgaagg ccgtgatgct ggccgccaac | 300 |
| gcgatcatgg cgggcgacgc cgagatcgtg gtggccggcg gccaggaaaa catgagcgcc | 360 |
| gccccgcacg tgctgccggg ctcgcgcgat ggtttccgca tgggcgatgc caagctggtc | 420 |
| gacaccatga tcgtcgacgg cctgtgggac gtgtacaacc agtaccacat gggcatcacc | 480 |
| gccgagaacg tggccaagga atacggcatc acacgcgagg cgcaggatga gttcgccgtc | 540 |
| ggctcgcaga acaaggccga agccgcgcag aaggccggca gtttgacga agatcgtc | 600 |
| ccggtgctga tcccgcagcg caagggcgac ccggtggcct tcaagaccga cgagttcgtg | 660 |
| cgccagggcg ccacgctgga cagcatgtcc ggcctcaagc ccgccttcga caaggccggc | 720 |
| acggtgaccg cggccaacgc ctcgggcctg aacgacggcg ccgccgcggt ggtggtgatg | 780 |
| tcggcggcca aggccaagga actgggcctg accccgctgg ccacgatcaa gagctatgcc | 840 |
| aacgccggtg tcgatcccaa ggtgatgggc atgggcccgg tgccggcctc caagcgcgcc | 900 |
| ctgtcgcgcg ccgagtggac cccgcaagac ctggacctga tggagatcaa cgaggccttt | 960 |
| gccgcgcagg cgctggcggt gcaccagcag atgggctggg acacctccaa ggtcaatgtg | 1020 |
| aacggcggcg ccatcgccat cggccacccg atcggcgcgt cgggctgccg tatcctggtg | 1080 |
| acgctgctgc acgagatgaa gcgccgtgac gcgaagaagg gcctggcctc gctgtgcatc | 1140 |
| ggcggcggca tgggcgtggc gctggcagtc gagcgcaaat aa | 1182 |

<210> SEQ ID NO 2
<211> LENGTH: 741
<212> TYPE: DNA
<213> ORGANISM: Artificial Sequence
<220> FEATURE:
<223> OTHER INFORMATION: gene coding acetoacetyl-CoA reductase (phaB)

<400> SEQUENCE: 2

| | |
|---|---|
| atgactcagc gcattgcgta tgtgaccggc ggcatggtg gtatcggaac cgccatttgc | 60 |
| cagcggctgg ccaaggatgg cttcgtgtg gtggccggtt gcggccccaa ctcgccgcgc | 120 |
| cgcgaaaagt ggctggagca gcagaaggcc ctgggcttcg atttcattgc ctcggaaggc | 180 |
| aatgtggctg actgggactc gaccaagacc gcattcgaca aggtcaagtc cgaggtcggc | 240 |
| gaggttgatg tgctgatcaa caacgccggt atcacccgcg acgtggtgtt ccgcaagatg | 300 |
| acccgcgccg actgggatgc ggtgatcgac accaacctga cctcgctgtt caacgtcacc | 360 |
| aagcaggtga tcgacggcat ggcgaccgt ggctggggcc gcatcgtcaa catctcgtcg | 420 |
| gtgaacgggc agaagggcca gttcggccag accaactact ccaccgccaa ggccggcctg | 480 |
| catggcttca ccatggcact ggcgcaggaa gtggcgacca agggcgtgac cgtcaacacg | 540 |
| gtctctccgg ctatatcgc caccgacatg gtcaaggcga tccgccagga cgtgctcgac | 600 |
| aagatcgtcg cgacgatccc ggtcaagcgc ctgggcctgc cggaagagat cgcctcgatc | 660 |
| tgcgcctggt tgtcgtcgga ggagtccggt ttctcgaccg cgccgactt ctcgctcaac | 720 |
| ggcggcctgc atatgggctg a | 741 |

<210> SEQ ID NO 3
<211> LENGTH: 1770
<212> TYPE: DNA
<213> ORGANISM: Artificial Sequence
<220> FEATURE:
<223> OTHER INFORMATION: gene coding PHB synthase (phaC)

-continued

```
<400> SEQUENCE: 3
atggcgaccg gcaaaggcgc ggcagcttcc acgcaggaag gcaagtccca accattcaag      60
gtcacgccgg ggccattcga tccagccaca tggctggaat ggtcccgcca gtggcagggc     120
actgaaggca acgccacgc ggccgcgtcc ggcattccgg gcctggatgc gctggcaggc     180
gtcaagatcg cgccggcgca gctgggtgat atccagcagc gctacatgaa ggacttctca     240
gcgctgtggc aggccatggc cgagggcaag gccgaggcca ccggtccgct gcacgaccgg     300
cgcttcgccg gcgacgcatg gcgcaccaac ctcccatatc gcttcgctgc cgcgttctac     360
ctgctcaatg cgcgcgcctt gaccgagctg gccgatgccg tcgaggccga tgccaagacc     420
cgccagcgca tccgcttcgc gatctcgcaa tgggtcgatg cgatgtcgcc cgccaacttc     480
cttgccacca atcccgaggc gcagcgcctg ctgatcgagt cgggcggcga atcgctgcgt     540
gccggcgtgc gcaacatgat ggaagacctg acacgcggca agatctcgca gaccgacgag     600
agcgcgtttg aggtcggccg caatgtcgcg gtgaccgaag gcgccgtggt cttcgagaac     660
gagtacttcc agctgttgca gtacaagccg ctgaccgaca aggtgcacgc gcgcccgctg     720
ctgatggtgc cgccgtgcat caacaagtac tacatcctgg acctgcagcc ggagagctcg     780
ctggtgcgcc atgtggtgga gcagggacat acggtgtttc tggtgtcgtg gcgcaatccg     840
gacgccagca tggccggcag cacctgggac gactacatcg agcacgcggc catccgcgcc     900
atcgaagtcg cgcgcgacat cagcggccag gacaagatca acgtgctcgg cttctgcgtg     960
ggcggcacca ttgtctcgac cgcgctggcg gtgctggccg cgcgcggcga gcacccggcc    1020
gccagcgtca cgctgctgac cacgctgctg gactttgccg acacgggcat cctcgacgtc    1080
tttgtcgacg agggccatgt gcagttgcgc gaggccacgc tgggcggcgg cgccggcgcg    1140
ccgtgcgcgc tgctgcgcgg ccttgagctg gccaatacct tctcgttctt gcgcccgaac    1200
gacctggtgt ggaactacgt ggtcgacaac tacctgaagg gcaacacgcc ggtgccgttc    1260
gacctgctgt tctggaacgg cgacgccacc aacctgccgg ggccgtggta ctgctggtac    1320
ctgcgccaca cctacctgca gaacgagctc aaggtaccgg gcaagctgac cgtgtgcggc    1380
gtgccggtgg acctggccag catcgacgtg ccgacctata tctacggctc gcgcgaagac    1440
catatcgtgc cgtggaccgc ggcctatgcc tcgaccgcgc tgctggcgaa caagctgcgc    1500
ttcgtgctgg gtgcgtcggg ccatatcgcc ggtgtgatca acccgccggc caagaacaag    1560
cgcagccact ggactaacga tgcgctgccg gagtcgccgc agcaatggct ggccggcgcc    1620
atcgagcatc acgcagctg gtggccggac tggaccgcat ggctggccgg gcaggccggc    1680
gcgaaacgcg ccgcgcccgc caactatggc aatgcgcgct atcgcgcaat cgaacccgcg    1740
cctgggcgat acgtcaaagc caaggcatga                                    1770
```